United States Patent [19]

Sanderson et al.

[11] Patent Number: 4,783,278

[45] Date of Patent: Nov. 8, 1988

[54] CONCENTRATED LIQUID COMPOSITIONS CONTAINING A PEROXYGEN COMPOUND

[75] Inventors: William R. Sanderson, Great Sankey Warrington; John D. Wharne, Halton Runcorn, both of England

[73] Assignee: Interox Chemicals Limited, London, England

[21] Appl. No.: 10,701

[22] Filed: Feb. 4, 1987

[30] Foreign Application Priority Data

Feb. 18, 1986 [GB] United Kingdom ............... 8603961

[51] Int. Cl.$^4$ .................... C11D 1/70; C11D 3/39; C11D 3/395

[52] U.S. Cl. ........................................ 252/95; 252/94; 252/99; 252/104; 252/DIG. 1; 252/186.26; 260/502 R; 568/31; 568/558; 568/559

[58] Field of Search ................ 260/502 R; 568/558, 568/559, 31; 252/DIG. 1, 104, 94, 99, 95

[56] References Cited

U.S. PATENT DOCUMENTS

| | | | |
|---|---|---|---|
| 4,100,095 | 7/1978 | Hutchins et al. | 252/99 |
| 4,483,781 | 11/1984 | Hartman | 252/174.12 |
| 4,536,313 | 8/1985 | Hignett et al. | 252/100 |
| 4,537,708 | 8/1985 | Downey et al. | 252/554 |
| 4,606,838 | 8/1986 | Burns | 252/94 |
| 4,615,820 | 10/1986 | Hepworth et al. | 252/139 |
| 4,704,404 | 11/1987 | Sanderson | 252/95 |
| 4,738,794 | 4/1988 | Harrison et al. | 252/95 |

FOREIGN PATENT DOCUMENTS 0124968  11/1984  European Pat. Off. ........ 260/502 R Primary Examiner—Paul Lieberman
Assistant Examiner—Ronald A. Krasnow
Attorney, Agent, or Firm—Larson & Taylor

[57] ABSTRACT

In general, inorganic or organic peroxyacids are unstable in the presence of a nonionic surfactant, so that it was not feasible to contemplate storing liquid compositions containing both components. It has now been discovered that storable compositions containing both components can be obtained by the use of particulate potassium-4-sulphoperoxybenzoic acid dispersed in the liquid nonionic surfactant containing phase. Additionally, the compositions can also include a dispersed particulate water-insoluble builder such as zeolite or water-soluble builder such as STPP. It is preferable to include a small amount of a chelating peroxidic stabilizer such as dipicolinic acid or 1,1,1-hydroxyethylidene diphosphonic acid.

18 Claims, No Drawings

CONCENTRATED LIQUID COMPOSITIONS CONTAINING A PEROXYGEN COMPOUND

The present invention relates to concentrated liquid peroxygen-containing compositions and more particularly to such compositions in which the peroxygen compound is a peroxyacid in particulate form therein.

Peroxyacids have been the subject of increased interest during recent years by virtue of their powerful oxidizing capacity which enables them to bleach household stains even at hand-hot washing temperatures and of their disinfectant and sanitizing properties which generally are superior to hydrogen peroxide-developing products under the same conditions. A contemporanious development has been the increased interest in liquid compositions for bleaching, washing or disinfection. Whilst it would be desirable to be able to offer liquid compositions containing peroxyacids, the art teaches that there are special difficulties for such compositions which result in the decomposition of the peroxyacid. Thus, for example, in U.S. Pat. No. 3,956,159 (May 1976) J. P. Jones teaches that it is very difficult to prepare stable liquid compositions containing peroxyacids as active bleaching component, due in part to the inherently unstable nature of peroxyacids which decompose at a rather rapid rate when placed in an aqueous medium in a solution containing other materials in combination with the highly reactive peroxyacid compounds. Subsequently at lines 33 to 37 the same patent teaches that it is the reactive nature of peroxyacids that presents special problems to the formulator upon storage of the bleach in liquid media. The patent subsequently teaches the use in combination of an anhydrous ternary mixture of t-butyl alcohol, ethylene diacetate and glycerol triacetate both stabiliser and pH buffer to yield a storage stable composition containing certain peroxyacids and their salts. Whilst these compositions exhibit peroxygen compound storage stability, especially in the absence of the suggested stabiliser system, they do not solve the problem of how to incorporate a peroxyacid in a liquid composition based upon a surfactant instead of merely an organic solvent. Thus, if, for example, Jones' Example 1 formulation is repeated but substituting an ethoxylated nonionic surfactant for his ternary mixture of solvents, the resultant mixture is unstable, the peroxyacid very rapidly losing its avox. In some trials over 95% avox was lost after a week.

When similar trials were conducted with other commercially available solid peracids, namely magnesium monoperoxyphthalate and potassium monopersulphate (KMPS) dispersed in a liquid non-ionic surfactant phase, similarly unstable compositions were obtained indicating that there is detrimental interaction between ethoxylated surfactants and peroxyacids, whether they be inorganic or organic, and in the case of the latter, either aromatic or aliphatic. It will accordingly be recognised that a reference in the background art to the incorporation of such peroxyacids in washing or bleaching compositions normally gives no reliable practical teaching about incorporating such peroxyacids in liquid systems based upon non-ionic surfactants because the background art descriptions were explicitly or implicitly relating to mixture of solid particles where the problem is markedly less acute than in liquids. In any event, the problem of peroxyacid/non-ionic surfactant interaction causing decomposition of the peroxyacid has only recently been identified, so that the inventors of the background art patents were unaware of it at the time that their descriptions were written. Additionally, it is not apparent that peroxyacids differ from persalts, ie percompounds that release hydrogen peroxide on dissolution in the effect of their interaction with nonionic surfactants. Persalts exhibit no significant decomposition on suspension in liquid surfactant formulations, whereas peroxyacids do. Accordingly, it is not feasible merely to substitute peroxyacids for sodium perborate in the disclosure of British Patent Specification No. 1 600 981 or U.S. Pat. No. 4,316,812 (Imperial Chemical Industries Ltd - Hancock et al) in view of the markedly impaired stability of peroxyacids compared with persalts.

Surprisingly a class of liquid nonionic surfactant-containing compositions having markedly improved stability has now been found by selection of the appropriate peroxyacid.

According to the present invention there are provided storable concentrated washing, bleaching or disinfectant compositions in which particulate potassium-4-sulphoperoxybenzoic acid is dispersed in an organic liquid carrier phase comprising a nonionic surfactant.

Herein, the term "potassium-4-sulphoperoxybenzoic acid" is often abbreviated to KSPB and refers to the product having the formula

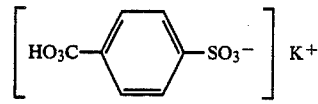

described and claimed in European Patent Specification No. 124968 (Interox Chemicals Limited). KSPB usually is employed as particles of less than 0.5 mm diameter and in many instances mainly of from 0.002 to 0.2 mm in diameter, in order to assist in dispersion of the solid particles throughout the liquid phase and the avoidance or substantial retardation of them settling out.

The organic liquid carrier may comprise a liquid nonionic surfactant or alternatively an organic solution of a solid nonionic surfactant. The nonionic surfactant suitably may comprise condensations of higher aliphatic alcohols or alkyl phenols or higher aliphatic acids with polyethylene oxide and/or polypropylene glycol. Typically, the higher alcohol or acids contains at least 8 up to 20 carbon atoms and from 5 to 15 carbon atoms in the alkyl moiety of the alkyl phenol, and in many instances the alcohol or acid is linear. In many products the alcohol or acids used is a narrow mixture of chain lengths, such as 9 to 11 carbon atoms, 10 to 12, 11 to 13, 12 to 14 or 13 to 15 and in preference the average chain length is in the range of from 9 to 15 linear carbon atoms. In general, the nonionic surfactant molecules contain a mean of at least 3 and normally less than 21 ethylene oxide and/or propylene oxide units in a hydrophilic moiety per alkyl moiety. In many suitable surfactants the number of ethylene oxide units is from 3 to 12, and also in others up to half may be replaced at random or terminally by propylene oxide units. The stability of KSPB in the presence of alcohol ethoxylates in which a minor portion in the region of 5 to 15% of terminal ethylene oxide groups have been replaced by propylene oxide groups has been found to be especially good even by comparison with other alcohol ethoxylates.

It will be recognised that a significant proportion of the non-ionic surfactants obtained from the combinations of the hydrophobic and hydrophilic moieties described herein are inherently liquid at ambient temperature and also that those which are solid can be liquified by dissolution in an appropriate organic solvent. It will also be understood that such solvents may be present as substitutes for part of the liquid nonionic surfactants to obtain a more convenient dose volume and can offer the formulator more scope for varying the ratio of solid to liquid active ingredients.

Solvents that can be employed include low molecular weight aliphatic alcohols such contain from 2 to 6 linear or non-linear carbon atoms, such as t-butanol, or low molecular weight ethylene glycol ether or propylene glycol ethers such as diethylene glycol dimethyl ether or monoethyl ether or ethylene glycol monobutyl ether or dipropylene glycol or esters or ethylene glycol esters such as mono or diacetate esters or glycerol esters such as glycerol triacetate.

Whilst the amount of organic solvent/extender that may be employed is at the discretion of the formulators, in many instances, the ratio of solvent:surfactant is not more than 4:1.

It will be recognised that the advantage of being able to suspend the peroxyacid in a surfactant is that the formulation gives a better cleansing performance, i.e. stain removal than if it is suspended or dissolved in an organic solvent alone.

Although the stability of the peroxyacid in the invention formulations is surprisingly good by comparison with other organic or inorganic peroxyacids, it can be further increased by incorporating within the liquid surfactant phase a trace amount of a complexing stabilising agent and in particular from aromatic hydroxy carboxylic acids such as dipicolinic acid or polyphosphonic acids such as 1-hydroxyethylene-1,1-diphosphonic acid. Other members of the classes of stabilising agents include respectively picolinic acid and quinolinic acid, and amino trimethylene phosphonic acid and alkylene amino methylene phosphonic acids of general formula $NX_3$ where X represents either a methylene phosphonic acid or ethylene amino bis methylene phosphonic acid group. The amount of agent or mixture of agents to use is often not more than 0.5% by weight of the composition and in a preferred range from 0.005 to 0.2% by weight. Particularly effective amounts used have been 0.01 and 0.1% by weight. By the use of the stabiliser, it has been found to be more practical to use for part of the liquid phase, liquid polyethylene glycols, such as those having a molecular weight of about 200 (i.e. 4 mers) up to about 500 (i.e. 12 mers).

Advantageously, it has also been found that the surfactant/KSPB compositions can additionally contain low alkaline builders, including in particular tripolyphosphates, such as sodium tripolyphosphate or alkali metal hydrogen phosphates, and zeolites particularly after calcination including especially zeolite A, sodium salt. The term low alkaline builder excludes high alkaline builders because the latter leads to an impairment of storage stability of KSPB that is unacceptable in practice. Although such built compositions tend to lose peracid available oxygen (avox) somewhat faster than corresponding unbuilt compositions it is surprising that they can exist for longer than a few days at all, in view of the fact that such peroxyacids in general are unable to survive in the hostile liquid environment generated by a combination of surfactant and builder. Accordingly, the practical upper limit of any solid builder is determined by the total solids content that can be suspended in the liquid phase, often around 50% by weight, and the amount of solid peroxyacid present. In many instances therefore the builder content is selected in the weight range of up to 40% and particularly of from 10 to 35%. Such proportions are often employed in conjunction with a KSPB content of from 5 to 20% by weight and especially 7 to 14%.

It will be recognised from the foregoing that the liquid phase normally comprises at least 50% by weight of the composition, and in most embodiments from about 55 to 95% of the weight. Thus, the proportion of non-ionic surfactant in the composition is normally not greater than 95% by weight, but by the use of solvents/extenders can be less than 50% by weight, conveniently often being at least 25% by weight.

In addition, the liquid phase can also contain one or more anionic surfactants and particularly alkyl-benzene sulphonate salts. Many of such anionic surfactants are solid at ambient temperatures and thus remain at least in part suspended in the liquid phase. The amount of anionic surfactant is usually not more than 20% by weight and often is from 5 to 15% by weight, particularly in conjunction with the aforementioned preferred concentrations of KSPB and optionally of builder. The composition by the inclusion of builder and/or anionic surfactant has enhanced washing performance when faced with a typical range of household stains in comparison with compositions containing simply KSPB in solvent and/or nonionic surfactant.

Additionally, the composition can with advantage contain one or more complexing builds such as amine carboxylates or hydroxy carboxylates. Examples of the former class include those of the formula $NY_3$ where Y represents a methylene carboxylate or carboxylic acid group or an ethylene amino bismethylene carboxylate or carboxylic acid group such as EDTA and NTA. Examples of the latter class include citrate/citric acid, and gluconate/gluconic acid. The amount of such complexing builders used is normally not greater than about 5% by weight but can be increased further if desired to replace all or part of or to supplement any inorganic builder that might be present.

The solids incorporated in the composition are preferably in fine powder form so as to reduce the likelihood of settling out. A mean particle diameter for each solid component is often below 0.1 mm and frequently from 0.02 to 0.1 mm.

Many of the invention compositions herein contemplated are readily poured and dissolve easily in aqueous solutions, except to the extent that insoluble zeolitic builder is used. Thus, the compositions can be used either undiluted or diluted with a little water for cleaning and disinfecting non-adsorbent surfaces such as walls, floors, work surfaces, vessels, baths, sinks and sanitaryware of metal, plastics, ceramics or glass, wood and rubber and, especially after dilution, to cleanse soiled adsorbent materials such as household laundry items or other articles made especially from cotton, rayon, flax or wool or man-made fibres such as polyesters or polyamides. The cleansing processes can be carried out at ambient temperature or at elevated temperature. The more preferred washing temperature for laundry is from 30° to 60° C. In laundry it is desirable to introduce sufficient washing composition to provide at least 5 ppm avox from the KSPB, and often from 10 to 50 ppm avox, ppm indicating parts per million by weight. This can often be provided by the use of composition selected in the range of 1 to 25 gpl, the selection taking into account the concentration of KSPB therein. In use, depending upon whether and the extent to which alkaline materials are present, especially builders, the compositions generate upon dissolution either a mildly acidic through to especially a mildly alkaline pH. It is preferred to generate a pH of from 7.5 to 9.5 to optimise bleaching/washing performance.

The washing processes for laundry can be carried out in currently available equipment. Washing times typically range from about 10 minutes to 30 minutes. Hand washing and extended steeping using solutions of the invention compositions can alternatively or additionally be used.

Having described the invention in general terms, specific embodiments will now be described more fully by way of example only.

EXAMPLES 1 TO 3 AND COMPARISONS A TO C

In these Examples and Comparisons, compositions were thoroughly mixed by shaking a powdered organic or inorganic peroxyacid (10% w/w) with a nonionic surfactant 90% w/w. The compositions were stored in small test tubes covered with polythene cap or a film (PARAFILM M - Trade Mark) at 32° C. in a dry environment. Samples were removed regularly and analysed for residual peroxyacid content, by the standard method of reacting with iodide and titrating the liberated iodine against thiosulphate quick. The test measures the available oxygen, sometimes abbreviated to Avox of the sample. The results are compared with the peroxyacid content of the composition before storage and the difference is expressed as a percentage of the figure before storage. It is designated Avox loss (%) in Table 1 below.

The peroxyacids and nonionic surfactants tested are designated as follows:

| | |
|---|---|
| Diperoxydodecanedioic acid | DPDDA |
| Potassium 4-sulphoperoxybenzoic acid | KSPB |
| 2KHSO$_5$.KHSO$_4$.K$_2$SO$_4$ (triple salt) | KMPS |
| t-butyl peroxybenzoic acid | tBPBA |
| Alcohol ethoxylate - C13/15, 11EO - SYNPERONIC A11 | A11 |
| Alcohol ethoxylate - C9, 9EO - ETHYLAN CD919 | CD 919 |
| Modified alcohol ethoxylate, C13/15, 7EO, 8% EO replaced by PO - SYNPERONIC 87K | 87K |

SYNPERONIC and ETHYLAN are Trade Marks of respectively ICI and Lankro Chemicals.

TABLE 1

| Ex/ Comp | Peracid | Nonionic | Avox Loss % after storage for (weeks) | | |
|---|---|---|---|---|---|
| | | | 1 | 2 | 4 |
| A1 | DPDDA | A11 | 96 | — | — |
| A2 | DPDDA | CD 919 | 95 | — | — |
| A3 | DPDDA | 87K | 26 | 44 | — |
| B1 | KMPS | A11 | 60 | — | — |
| B2 | KMPS | CD 919 | 25 | — | 63 |
| B3 | KMPS | 87K | 75 | — | — |
| C1 | tBPBA | A11 | 96 | — | — |
| C2 | tBPBA | CD 919 | 96 | — | — |
| C3 | tBPBA | 87K | 95 | — | — |
| Ex 1 | KSPB | A11 | 3 | 11 | 33 |
| Ex 2 | KSPB | CD 919 | 11 | 24 | 36 |
| Ex 3 | KSPB | 87K | 0 | 0 | 0 |

From Table 1 it can be seen that the stability of KSPB was substantially better than any of the comparison compositions. Thus, whilst the best of the comparisons was probably DPDDA in 87K, the peroxyacid loss was 44% in 2 weeks whilst KSPB in 87K had lost no peracid avox in the same period. Indeed, it has lost none after 10 weeks storage. Clearly, the performance of KSPB was not simply ascribable to the fact that it was a potassium salt in view of the fact that KMPS was markedly less stable and likewise it could not be ascribed to the fact that the peroxybenzoic acid nucleus is substituted in the para position by a bulky substituent since KSPB shares that feature with tBPBA.

When Example 1 was repeated with the addition of 0.01 parts by weight dipicolinic acid (DPA), the rate of loss of avox fell to 29% in 8 weeks. Similar or better avox stability was achieved when the surfactant in Example 1 was substituted by the corresponding ethoxylate of 7EO units instead of 11EO units, or by an alcohol ethoxylate C9-11, 8EO units available under the Trade Mark NEODOL 91-8, or by two alcohol ethoxylate/propoxylates, one C$_9$, 6EO/4PO units at random, ETHYLAN CD964, and the other C$_{12-14}$, 6EO/6 terminal PO units, ETHYLAN CPG 660.

EXAMPLES 4 AND 5

Example 2 was repeated but additionally incorporating in Ex 4 0.1% w/w dipicolinic acid and in Ex 5 0.1% t.q. 1-hydroxyethylene 1,1-diphosphonic acid (DEQUEST 2010). The stability increased to register no loss of avox after 10 weeks storage of Ex 4 at 32° C. and only 3% loss after 12 weeks storage at 32° C. for Ex 5.

EXAMPLE 6

Example 3 was repeated but modified by substituting a mix of 6 parts polyethylene glycol (PEG) 200, 1 part SYNPERONIC A3 (C13/15, 3EO) and 3 parts SYNPERONIC 87K for the 87K. It was found that the mixture lost 32% avox after 8 weeks storage at 32° C. indicating that liquid polyethylene glycols can be employed as diluents in the invention compositions.

The suitability of other diluents for the liquid phase can be seen from the following stability data. A dispersion of 10% KSPB in 90% w/w solvent was stored at 32° C. as in the preceding examples. After 10 weeks storage only 9% avox had been lost from a dispersion in dipropylene glycol, 0% from ethylene glycol monoacetate and ethylene glycol diacetate in 8 weeks and 0% from t-butanol in 4 weeks. It can be seen that low molecular weight aliphatic esters and ethers are suitable organic liquid diluents, if such is desired.

EXAMPLE 8

In this Example mixtures containing a builder (sodium tripolyphosphate - STPP) were made by shaking vigorously 10 parts by weight KSPB with 60 parts by weight 87K liquid nonionic surfactant and 30 parts by weight STPP powder (EMPIPHOS STP/D - Albright and Wilson). The compositions were stored as before at 32° C. and their avox determined at intervals. 11 series of trials were made using 9 different batches of KSPB, and showed some variation in stability. 4 series terminated after 5 weeks storage, 3 showing avox losses of below 15% and the worst a loss of 48%. Of the 7 remaining series, measured after 8/9 weeks storage, four series had lost less than 25% avox, one series about 39%, one series 75% although after 4 weeks only 14% had been lost and in the last 95% avox. It can be seen that the compositions with one exception or possibly two were regularly stable despite the presence of a high proportion of an alkaline builder therein. Further investigation has indicated that the analytical technique employed can itself cause loss of avox from peracid compositions, but only if they also contain an alkaline builder and if the builder is not acidified quickly enough. It is not believed that the odd very high apparent loss of avox was caused in that way.

In a further series of trials on more samples of the this composition, carried out in triplicate, the compositions had lost between 21 and 25% of the avox after 12 weeks storage.

EXAMPLE 9

In this Example, further STPP-containing compositions were made like those of Example 8 but employing CD 919 approx 60 parts by weight and 0.01 parts by weight DEQUEST 2010 instead of the 87K. 13 series of trials were conducted. Of these, 5 terminated at 4/5 weeks storage of which 3 has lost virtually no avox (below 5%), one 11% and one 80%. Of the remaining 8 that terminated after 8 or 9 weeks, 5 had lost less than 25%, 2 between 25 and 35% and the last one 65% (21% after 4 weeks). It can once again be seen that the compositions are generally very stable, and the odd spuriously high loss arose by virtue of avox loss during the analysis.

EXAMPLE 10

In this Example, calcined zeolite A, sodium salt, 30 parts by weight, was substituted for all the STPP in the composition of Example 9. After 9 weeks storage at 32° C., 2 samples had each lost 25/26% avox demonstrating that the zeolite was eminently suitable for KSPB compositions.

EXAMPLE 11

In this Example, the washing performance of the composition of Example 3 was determined and compared with a simple solution of 10% KSPB in a mixture of solvents, GTA, EGMA, t-BOH. Swatches of white cotton prestained with coffee, blackberry, tea, red wine, EMPA112 or EMPA101 were washed at 40° C. for 20 minutes in a solution of liquid composition at 4 gpl in municipal water (about 100–120 ppm hardness as $CaCO_3$) the natural pH of the solution in a *** machine. After being washed, each swatch was rinsed with cold water and air dried. The reflectance of each swatch was then determined (RW) and by comparison with the reflectance of the unstained swath (RB) and the prewash stained swatch (RS) the extent of stain removal calculated using the fraction $(R_w - R_b)/(R_s - R_b)$.

It was found that on the six stains the average stain removal of the invention compositions was 52% whereas using the comparison product it was only 47%.

We claim:

1. Storable concentrated liquid washing, bleaching or disinfectant compositions in which particulate potassium-4-sulphoperoxybenzoic acid (KSPB) is dispersed in an organic liquid carrier phase which comprises a nonionic surfactant, said organic liquid carrier phase comprising at least 50% by weight of the composition based on the weight of the composition.

2. A composition according to claim 1 in which the nonionic surfactant is a condensation product of higher aliphatic alcohols or alkyl phenols or higher aliphatic acids with at least one of polyethylene oxide and polypropylene oxide.

3. A composition according to claim 1 in which the nonionic surfactant contains a mean of from 3 to 21 ethylene oxide and/or propylene oxide units.

4. A composition according to claim 2 in which the alkyl residue of the alcohol or acid moiety in the surfactant has an average carbon chain length of 9 to 15 carbon atoms.

5. A composition according to claim 1 in which the liquid carrier phase contains a solvent selected from $C_2$ to $C_6$ aliphatic alcohols, low molecular weight ethylene glycol ethers or esters or propylene glycol ethers or esters and a glycerol esters.

6. A composition according to claim 5 in which the solvent is ethylene glycol mono- or di- acetate, t-butanol, diethylene glycol mono or dimethyl ether or ethylene glycol monobutyl ether.

7. A composition according to either of claims 5 or 6 in which the weight ratio of solvent:surfactant is not greater than 4:1.

8. A composition according to claim 1 in which the KSPB particles have a diameter of below 0.5 mm.

9. A composition according to claim 1 or 8 which contains from 5 to 20% by weight KSPB.

10. A composition according to claim 1 or 5 which contains an effective amount of a complexing stabiliser.

11. A composition according to claim 10 in which the stabiliser is selected from the group consisting of aromatic hydroxy carboxylic acids and polyphosphonic acids.

12. A composition according to claim 11 in which the stabiliser is selected from the group consisting of dipicolinic acid, quinolinic acid, and a compound having the formula $NX_3$ in which X represents a methylene phosphonic acid or an ethylene amino bis methylene phosphonic acid group.

13. A composition according to claim 1 or 5 which contains up to 15% by weight of an anionic surfactant.

14. A composition according to claim 1 which contains additionally a low alkaline builder dispersed in the liquid phase.

15. A composition according to claim 14 in which the builder is selected from the group consisting of an alkali metal tripolyphosphate, an alkali metal hydrogen phosphate, a zeolite, a calcined zeolote, an amine carboxylate complexing builder, and an hydroxy carboxylate complexing builder.

16. A composition according to claim 14 or 15 characterised in that the amount of builder is from 10 to 35% by weight.

17. A composition according to claim 1 which comprises from 5 to 20% by weight KSPB and 10 to 35% by weight of a builder selected from the group consisting of alkali metal tripolyphosphates, alkali metal hydrogen phosphates and a zeolite dispersed in a liquid phase which comprises a nonionic surfactant which is selected from the group consisting of liquid condensation products of higher aliphatic alcohols or alkyl phenols or higher aliphatic acids with at least one of polyethylene oxide and polypropylene oxide and which phase includes 0 to 15% by weight of an anionic surfactant and 0 to 4 parts by weight of a solvent per part by weight of surfactant, said solvent being selected from $C_2$ to $C_6$ aliphatic alcohols, low molecular weight ethylene glycol ethers or esters or propylene glycol ethers or esters and glycerol esters, % by weight being based on the composition weight.

18. A composition according to claim 17 in which the solid suspended particles have a mean particle diameter of from 0.02 to 0.1 mm.

* * * * *